United States Patent [19]

Olson

[11] Patent Number: 5,409,009

[45] Date of Patent: Apr. 25, 1995

[54] METHODS FOR MEASUREMENT OF ARTERIAL BLOOD FLOW

[75] Inventor: Walter H. Olson, North Oaks, Minn.

[73] Assignee: Medtronic, Inc., Minneapolis, Minn.

[21] Appl. No.: 215,070

[22] Filed: Mar. 18, 1994

[51] Int. Cl.$^6$ ............................................. A61B 8/12
[52] U.S. Cl. ................................ 128/661.08; 607/23; 128/734
[58] Field of Search .................... 128/661.08, 661.09, 128/661.10, 662.01, 662.06, 734; 607/4, 5, 6, 23, 24

[56] References Cited

U.S. PATENT DOCUMENTS

| | | | |
|---|---|---|---|
| 3,614,955 | 10/1971 | Mirowski et al. | 128/419 D |
| 4,589,419 | 5/1986 | Laughlin et al. | 128/663 |
| 4,598,716 | 7/1986 | Hileman | 128/663 |
| 4,686,987 | 8/1987 | Salo et al. | 128/419 PG |
| 4,730,619 | 3/1988 | Koning et al. | 128/419 PG |
| 4,733,667 | 3/1988 | Olive et al. | 128/419 PG |
| 4,770,177 | 9/1988 | Schroeppel | 128/419 PG |
| 4,774,950 | 10/1988 | Cohen | 128/419 D |
| 4,791,931 | 12/1988 | Slate | 128/419 PG |
| 4,805,621 | 2/1989 | Heinze et al. | 128/419 PG |
| 4,867,160 | 9/1989 | Schaldach | 128/419 PG |
| 4,899,751 | 2/1990 | Cohen | 128/419 PG |
| 4,967,749 | 11/1990 | Cohen | 128/419 PG |
| 5,137,019 | 8/1992 | Pederson et al. | 128/734 |
| 5,139,020 | 8/1992 | Koestner et al. | 128/662.06 |
| 5,203,337 | 8/1993 | Feldman | 128/661.09 |
| 5,316,001 | 5/1994 | Ferek-Petric et al. | 128/662.06 |

OTHER PUBLICATIONS

Tacher, et al, "Perivascular impedance sensors for in vivo chronic blood pressure measurement: Detection systems for automatic defibrillators, cardioverters and blood pressure controllers" 37th ACEMB, Sep. 17–19, 1984, p. 20.

Konrad, et al., "A New Implantable Arterial Pulse Sensor for Detection of Ventricular Fibrillation" *Medical Instrumentation*, AAMI, vol. 22 (6), pp. 304–311.

Primary Examiner—George Manuel
Attorney, Agent, or Firm—Reed A. Duthler; Harold R. Patton

[57] ABSTRACT

A sensor for measurement of one or more parameters of arterial blood flow, located on a transvenously inserted lead. The sensor may be inserted into a vein that is anatomically adjacent to the artery in which blood flow parameters are to be monitored, rather than into the artery itself. The sensor may take the form of a set of spaced electrodes for impedance plethysmography, a piezoelectric pulse sensor or a pulse Doppler sensor for detecting arterial blood flow. By measuring arterial blood flow from an adjacent vein, problems associated with insertion of the sensor into the arterial system may be avoided. The sensor may be used to control the characteristics of an implantable device, such as an implantable pacemaker/cardioverter/defibrillator, an implantable drug dispenser or a rate responsive pacemaker.

6 Claims, 4 Drawing Sheets

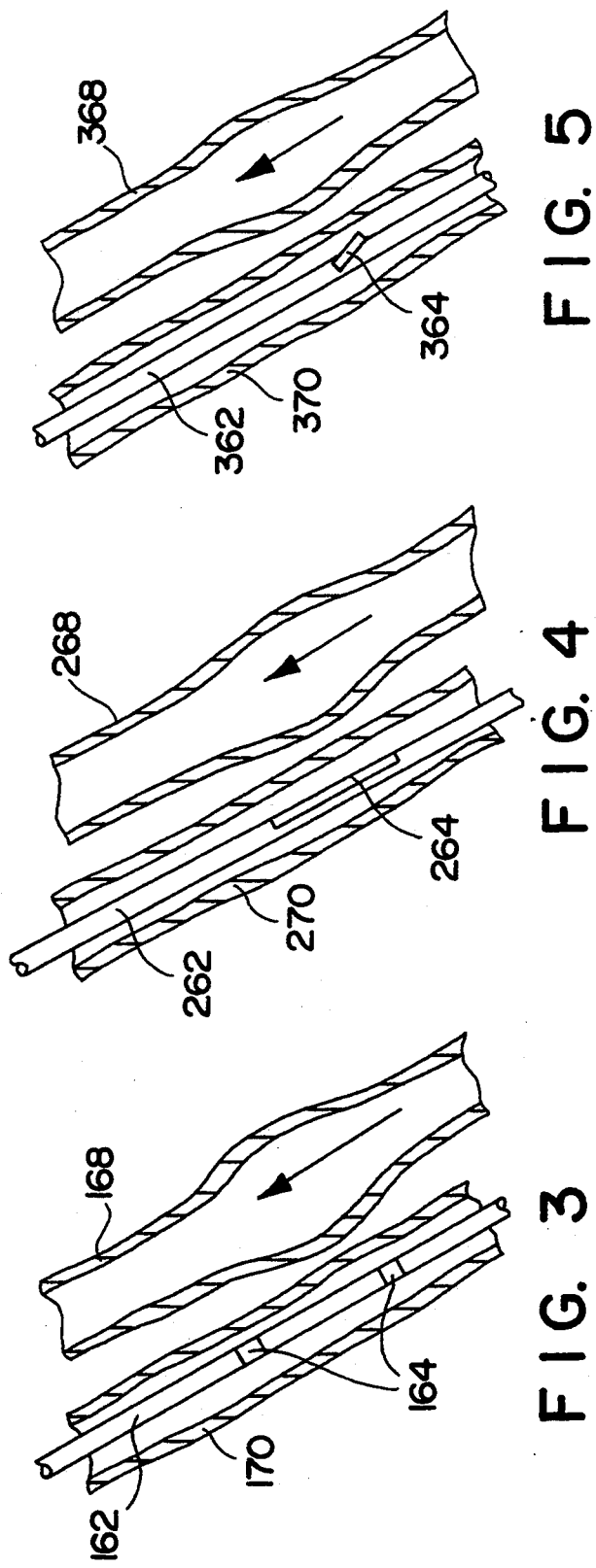

METHODS FOR MEASUREMENT OF ARTERIAL BLOOD FLOW

BACKGROUND OF THE INVENTION

This invention relates generally to sensors for measurement of aerial blood flow parameters and more specifically to the use of such sensors to control the operation of implantable medical devices.

In a number of medical and surgical procedures, it is desirable to monitor parameters of aerial blood flow at specific locations within the aerial system, in the course of diagnostic testing or monitoring of cardiovascular system performance. Aerial blood flow parameters may also be employed to control the operation of an implantable device. For example, it is known that an inverse relationship exists between aerial blood pressure and heart rate and that the baroreceptor reflex causes changes in cardiac rate to provide short term control of aerial blood pressure. In a heart which exhibits bradycardia or disassociation between the ability of the heart to increase cardiac output in response to physical exercise, it is desirable to provide cardiac pacing in order to adjust heart rate to physiologic demand in a manner similar to the human body's natural baroreceptor reflex. An aerial blood pressure sensor, for example, may be used to control the pacing rate in such a device.

It is also shown that high ventricular tachycardias and ventricular fibrillation have marked effects on hemodynamic performance and that the comprise in hemodynamic performance may be most efficaciously measured in the aerial vascular system. Aerial blood flow parameters are recognized as being useful in this context to assist in controlling the operation of anti-tachycardia devices.

The direct measurement of aerial blood flow parameters using sensors introduced into the left ventricle or the aerial system has been proposed, but is not presently practiced in the context of conically implantable devices. The primary concern is that the introduced sensor may provoke thrombus formation and/or embolization due to the difficulty of providing a high pressure seal at the point of entry to the chamber or artery. Moreover, chronic implantation often involves the accumulation of fibrotic material on the sensors leading to possible obstruction of the artery. In addition, clots formed on the sensor may break free, raising the risk of stroke. In order to avoid these problems, the use of a perivascular transducer placed adjacent to or around the exterior vascular wall of the selected artery has been proposed. However, such a device may itself poses the risk of erosion and rupture of the artery or constriction of the artery either directly or by tissue growth around the transducer.

Nonetheless, chronically implantable sensors for measuring arterial blood flow parameters for control of implantable devices continue to be proposed, indicating the desirability of obtaining measurements of arterial blood flow parameters, in conjunction with controlling such devices. For example, U.S. Pat. Nos. 4,774,950 and 4,967,749 issued to Cohen and the articles "Perivascular Impedance Sensors for In Vivo Chronic Blood Measurement: Detection Systems for Automatic Defibrillators, Cardioverters and Blood Pressure Controllers" by Tacker et al., published in the proceedings of the 37th ACEMB, September, 1984, page 20 and "A New Implantable Arterial Blood Sensor for Detection of Ventricular Fibrillation" by Konrad et al, published in *Medical Instrumentation*, December, 1988, Vol. 22(6): 304-311 disclose sensors for measurement of arterial blood flow. The Cohen patents envision mounting of an indwelling pressure transducer in the left ventricle or an artery, and disclose the use of measured left ventricular or arterial blood pressure to control an implantable device such as a cardiac pacemaker or anti-tachycardia device. The Tacker and Konrad articles suggest that placing the transducer within the arterial system as suggested in the Cohen is disadvantageous, and therefore suggests pulse sensors located adjacent to the carotid and femoral arteries, employing impedance plethysmography to measure pulsatile blood flow, for use in detection of ventricular fibrillation and ventricular tachycardias leading to hemodynamic compromise.

U.S. Pat. No. 4,791,931 issued to Slate discloses a pressure transducer for measurement of blood pressure adjacent to an easily accessible artery, for use in controlling the rate of a rate responsive cardiac pacemaker. A similar system is disclosed in U.S. Pat. No. 4,899,751 issued to Cohen, which employs intravascular pressure transducers similar to those disclosed in the Cohen '749 patent cited above. The Cohen patents, the Slate patent, and the cited Konrad and Tacker articles are indicative of the types of devices with which sensors manufactured and used according to the present invention may usefully be employed, and are all incorporated herein by reference in their entireties.

SUMMARY OF THE INVENTION

The present invention provides an arterial blood parameter sensor mounted on a permanently implantable lead. However, rather than inserting the lead into the artery in which flow parameters are to be measured, the lead is inserted into a vein adjacent to the artery, and located adjacent to the point in the artery at which the measurement is desired. At many positions within the body, arteries and veins are adjacent and parallel to each other, so that the exact position of the sensor in the vein is not critical. The sensor is adapted to measure flow in the adjacent artery, rather than in the vein in which the sensor resides. This approach to measuring arterial blood parameters avoids the difficulties attendant to placement of a sensor in the artery, without requiring a more invasive procedure to locate the sensor in muscle tissue adjacent the artery, or to mount the sensor around the artery. This approach also avoids difficulties associated with long term implant of sensors mounted in or around arteries. The sensors may be mounted on a transvenous pacing, sensing or cardioversion lead extending from an implanted pulse generator, and into the desired location in the venous system. The sensors may take the form of a spaced electrode pair or pairs for impedance plethysmography, a piezoelectric or other pressure sensor, a pulse Doppler ultrasound sensor or other sensor for measuring flow of blood through the adjacent artery. The measured arterial blood flow parameter may be employed by the implanted device to control pacing rate, to initiate or select the type of antiarrhythmic therapy delivered by an implantable pacemaker/cardioverter/defibrillator or may be used to control the timing and/or dosage of a drug delivered by an implantable drug dispenser.

BRIEF DESCRIPTION OF THE DRAWINGS

FIG. 3 illustrates an impedance pulse sensor, installed in a vein, adjacent to an artery in which pulsatile arterial flow is to be detected.

FIG. 4 illustrates a piezoelectric pressure sensor on a lead located in a vein adjacent to an artery within which arterial blood pressure pulses are to be measured.

FIG. 5 is an illustration of a pulse Doppler ultrasound transducer on a lead located in a vein adjacent to an artery within which arterial blood flow and velocity is to be measured.

DETAILED DESCRIPTION OF THE PREFERRED EMBODIMENTS

Figure 1:
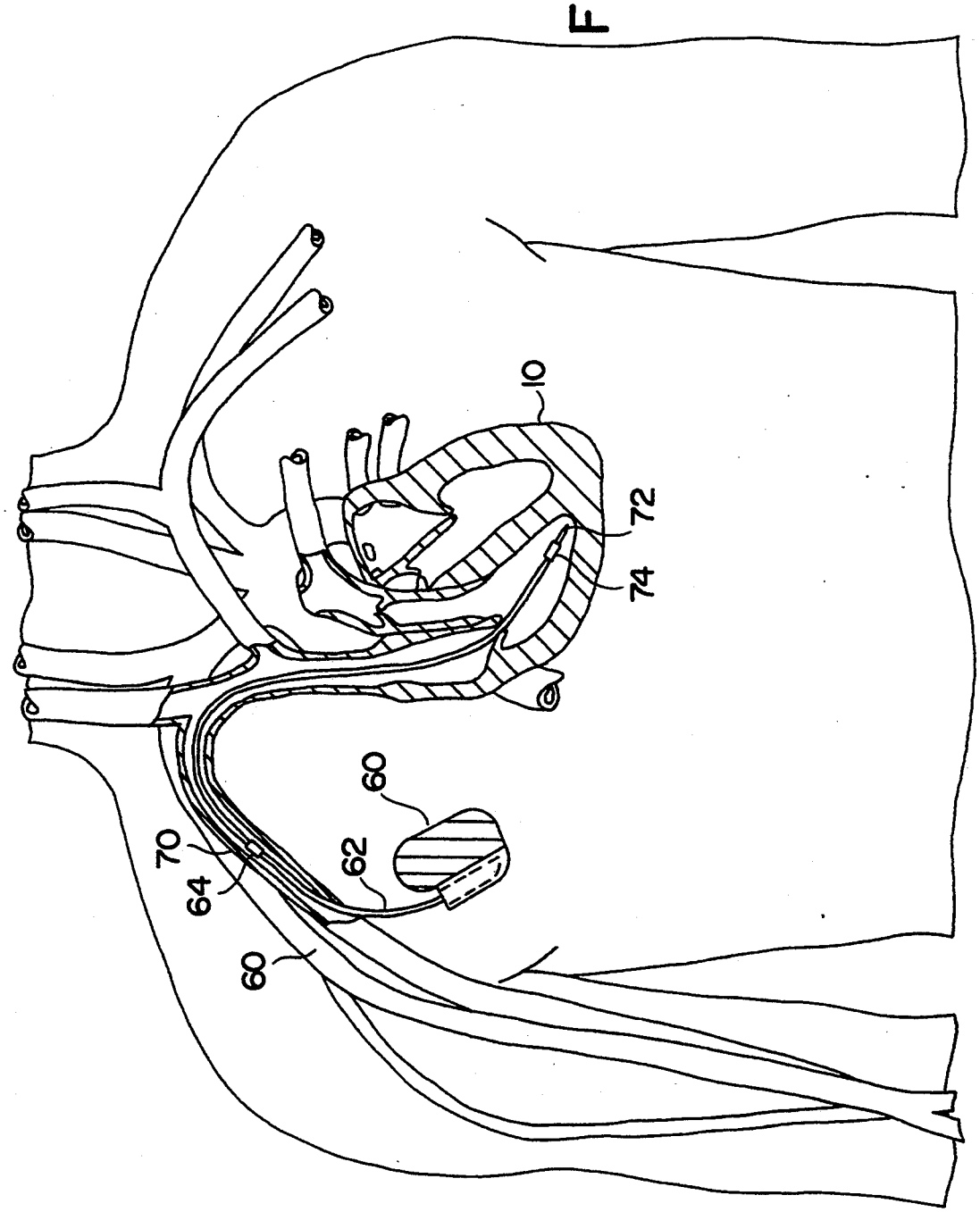
FIG. 1 is a diagram of a rate responsive cardiac pacemaker, as implanted, employing the present invention and illustrating the venous location of the arterial pressure, pulse or flow sensor.
Figure 2:
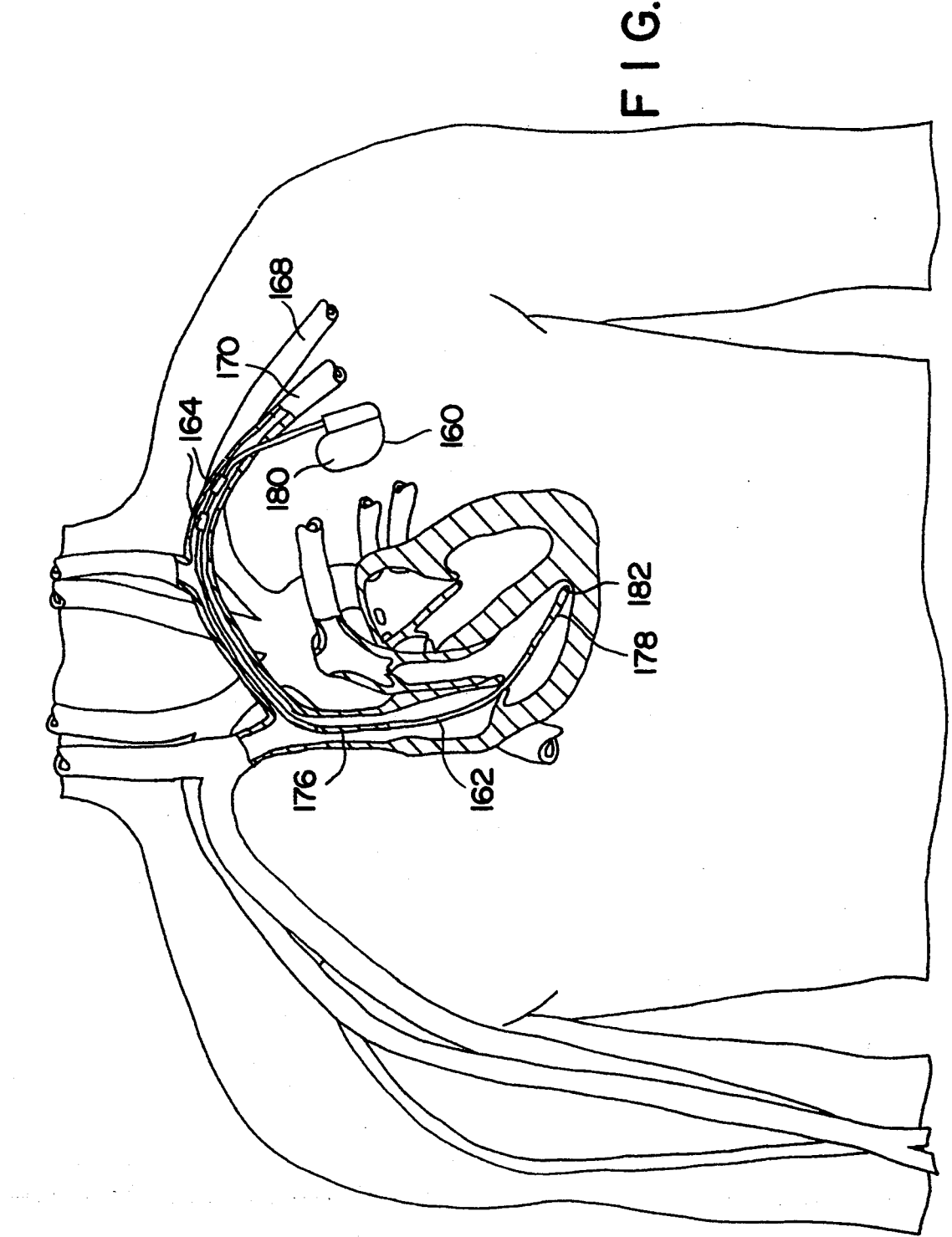
FIG. 2 is a diagram illustrating a tachyarrhythmia control device as implanted, illustrating a venous location of the arterial pressure, pulse or flow sensor.

FIGS. 1 and 2 illustrate the installation of a cardiac pacemaker and an implantable antiarrhythmia device, respectively, employing arterial blood parameter sensors according to the present invention. These drawings also illustrate the heart and the interrelation of some of the major arteries and veins that enter and exit the heart.

The major veins and arteries that enter and exit the heart are typically paired, located adjacent to one another. In particular, veins through which transvenous pacing and cardioversion leads are typically implanted are paired in side by side relation to a corresponding artery. For example, FIG. 1 illustrates the pairing of the right axillary vein 70 with the parallel and adjacent right proximal axillary artery 68. Similarly, FIG. 2 illustrates the corresponding pairing of the left axillary vein 170 and the left proximal axillary artery 168. The internal jugular veins are located adjacent the corresponding carotid arteries, and also provide potential locations for sensors employed according to the present invention.

Blood pressure within the venous system is on average much lower than the pressure within the arterial system. Vein and artery walls are constructed differently, with the venous wall typically thinner and less muscular than the wall of the adjacent paired artery. Further, while venous blood pressure is relatively steady during a cardiac cycle, the arteries exhibit substantial pulsatile pressure variations, corresponding to individual heart beats, causing distension of the arterial walls. These factors allow the various sensors of the present application to effectively measure atrial pressure and blood flow parameters from an adjacent vein in spite of blood flow in the opposite direction through the vein.

As illustrated in FIG. 1, a first embodiment of the present invention has two primary components including a cardiac pacemaker 60 and a lead 62 which carries pacing electrodes 72 and 74 and a sensor or sensors 64 located on the lead body within a vein 70 (in this case the right axillary vein) located adjacent the artery 68 in which blood flow parameters are to be measured. The pulse generator 60 is shown implanted subcutaneously in a conventional fashion in the right pectoral region, with lead 62 extending through an incision in axillary vein 70, and having its distal end located in the right ventricle of the heart 10. Sensors 64 are illustrated adjacent to the right proximal axillary artery 68, in which blood flow parameters are to measured. It should be noted that in an installation such as this, the axillary vein is typically tied off, and tied around the lead 62, preventing any substantial blood flow through the axillary vein in that immediate area. If the sensors 64 are located closely adjacent the site of venous insertion of the lead 62, therefore, there will be no substantial flow of blood through the vein in the vicinity of the sensors. Alternatively, if the sensors 64 are located a substantial distance from the site of venous insertion or if the sensors are mounted on a separate lead, and located in a vein, (e.g., the jugular vein) differing from the vein through which the lead carrying sensors is inserted, it is to be expected that there will be blood flow through the vein, adjacent the sensor. However, because of the relatively non-pulsatile nature of venous blood flow, this factor will not prevent sensing of the more pulsatile blood flow in the adjacent artery.

FIG. 2 illustrates an alternative embodiment of the present invention in which the arterial blood flow parameter sensing lead 162 is employed in conjunction with an implantable pacemaker/cardioverter/defibrillator 160. As illustrated, the defibrillator 160 is implanted in the left pectoral region, with the lead 162 carrying sensors 164 extending through the left axillary vein 170, which is adjacent to the left axillary artery 168.

In the illustrated embodiment, the pacemaker/cardioverter/defibrillator 160 is provided with an electrode 180 located on the external housing of the device, which in use is mounted facing the heart tissue. The lead 162 also includes defibrillation electrodes 176 and 178 and one or more pacing and sensing electrodes 182, for sensing ventricular depolarizations and for pacing the heart. As illustrated, the sensors 164 take the form of a pair of electrodes used for impedance plethysmography for determining the magnitude, presence or absence of pulsatile arterial blood flow for use in selecting between various therapies to be delivered by the implantable pacemaker/cardioverter/defibrillator 160.

FIGS. 3–5 are illustrations of alternate sensors which may be employed in the context of the present invention. FIG. 3 illustrates an impedance plethysmograph-type sensor. FIG. 4 illustrates a piezoelectric or piezoresistive pressure sensor and FIG. 5 illustrates an ultrasonic pulse Doppler or ultrasonic transit-time sensor. Any one of these sensors may be mounted within a vein and used to sense the amplitude, presence or absence of pulsatile flow in an adjacent artery, in conjunction with either a pacemaker or an implantable pacemaker/cardioverter/defibrillator as illustrated in FIGS. 1 and 2, respectively.

FIG. 3 illustrates an impedance sensor, particularly valuable for use in conjunction with an implanted pacemaker/cardioverter/defibrillator. As discussed in the above-cited Tacker et al and Konrad et al. articles, two or more electrodes placed in extra-vascular tissue adjacent to an artery may be used in the fashion of an impedance plethysmograph to monitor the pulsatile flow of blood through the artery. As illustrated, the sensors and the associated artery and vein correspond to those illustrated in FIG. 2. The lead 162 is shown mounted within a vein 170, which passes adjacent to an artery 168 in the general vicinity of the sensing electrodes 164. As illustrated, the wall of the artery 168 bulges in response to flow of blood through the artery. In the drawing, the bulge is illustrated in an exaggerated and fixed fashion, in order to illustrate the fact that the volume of conductive fluid (blood) within the field of the electrodes will vary as a function of pulsatile flow through the artery 168, and thus may be readily measured using standard impedance plethysmography methods. Two, three or more electrodes may be used in order to perform this measurement, as discussed in the above-cited Tacker et al and Konrad et al articles.

FIG. 4 illustrates an alternative sensor for use in conjunction with the present invention. A lead 262 carrying a piezoelectric sensor 264 is mounted within a vein 270. The sensor 264 is located at a point at which an adjacent artery 268 is close to the vein 270. The bulging of the arterial wall, illustrated in exaggerated form, provides a pulsatile pressure signal which may be detected from sensor 264. Sensor 264 may be, for example, a piezoelectric bimorph as described in U.S. Pat. No. 4,770,177 issued to Schroeppel et al., incorporated herein by reference in its entirety. Unlike the Schroeppel reference, however, the pressure sensor is not intended to sense changes in venous diameter, which occur at a much slower rate and lesser amount than the human heart beat, but instead is adapted to sense the pulsatile signal provided by the adjacent artery 268, which occurs as a result of each heartbeat.

FIG. 5 illustrates yet another alternative embodiment of the present invention. In FIG. 5, a piezoelectric crystal 364 is mounted to an electrical lead 362 in order to function as a flow sensor. The lead is mounted in a vein 370, and the crystal is directed toward the adjacent artery 368. The crystal may operate as a pulse Doppler transducer for monitoring blood flow, as discussed in U.S. Pat. No. 4,589,419, issued to Laughlin et al., incorporated herein by reference in its entirety. However, unlike the sensor illustrated in the Laughlin et al. patent, the pulse Doppler crystal is not located within the artery in which blood flow is to be monitored but is instead mounted within the adjacent vein. Electronic processing of Doppler ultrasound signals can be used to differentiate the direction of flow in the artery, which is opposite to the direction of flow in the vein. In this embodiment of the invention, it is beneficial to have the crystal located as close to the side of the vein wall as possible, and directed toward the adjacent artery.

In order to prevent changes in venous blood vessel diameter and venous blood flow parameters from effecting the sensor, in the embodiments illustrated in FIGS. 3, 4 and 5, it is beneficial to high pass filter (e.g. eliminate signals below about 10 Hz) the output the sensors to eliminate all but the pulsatile signals associated with blood flow through the adjacent artery 268.

Figure 6:
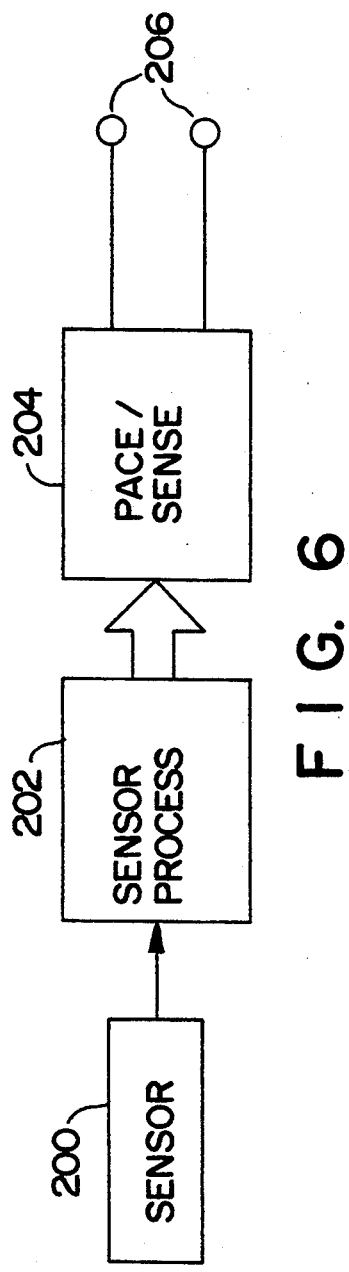
FIG. 6 is a block functional diagram of an implantable rate-responsive pacemaker employing the present invention.
Figure 7:
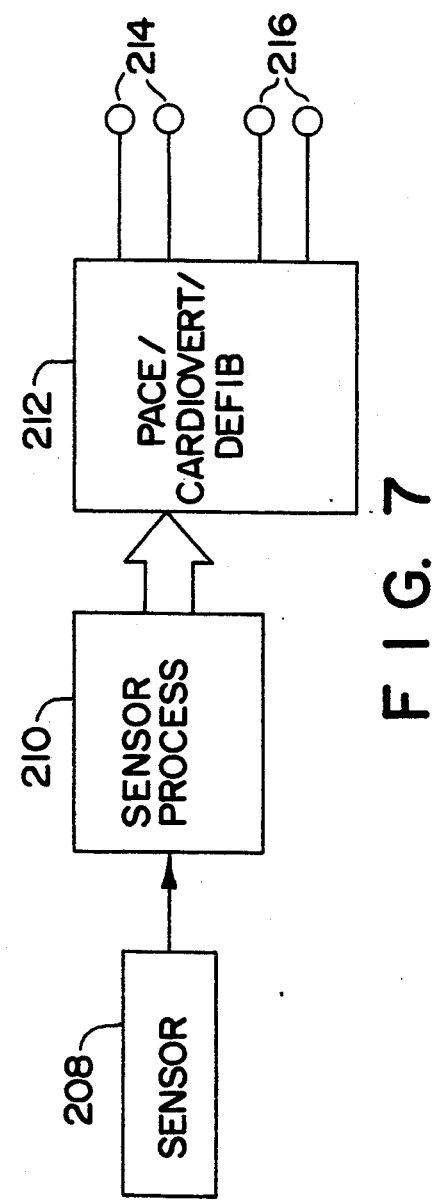
FIG. 7 is a block functional diagram of an implantable pacemaker/cardioverter/defibrillator employing the present invention.

FIGS. 6 and 7 are block functional diagrams illustrating the integration of the sensors illustrated in FIGS. 3-5 into implantable pacemakers and implantable pacemaker/cardioverter/defibrillators. Because the various components of the block diagrams in FIGS. 6 and 7 are described in detail (although not in combined form) in the prior art patents and publications cited below, the specific circuitry and structure employed to implement the functional subassemblies is described. However, their general organization and function is as follows.

FIG. 6 illustrates an implantable pacemaker in which a sensor 200, which may correspond to any of the sensors illustrated in FIGS. 3-5 is coupled to sensor processing circuitry 202 to provide a signal for controlling the operation of pacing circuitry 204, to vary the pacing rate of pacing pulses applied to pace/sense electrodes 206. For example, in the event that the sensor 200 takes the form of piezoelectric pressure sensor, the sensor processing circuitry 202 and pacing circuitry 204 may correspond to those disclosed in U.S. Pat. No. 4,730,619 Koning et al., incorporated herein by reference in its entirety. As in the Koning patent, the pulsatile pressure signal may be measured and used to address a look up table to determine an appropriate corresponding pacing rate. In a fashion analogous to the Koning patere, a substantial increase in the peak pulsatile pressure or peak rate of pressure change (dP/dt), without corresponding increase in the heart rate detected by the pacing circuitry 204 via the pace/sense electrodes 206 should trigger an increase in the rate of pacing pulses provided by pacing circuitry 204.

In the event that the sensor 200 takes the form of an impedance plethysmograph type sensor, as described in the above cited Konrad and Tacker et al. articles, the sensor processing circuitry 202 may take the form of any number of impedance plethysmograph circuits described in the prior art, for use in conjunction in with cardiac pacemakers. For example, in the event that two electrodes are used as an impedance sensor, processing circuitry as disclosed in U.S. Pat. No. 4,805,621 issued to Heinze et al. may be employed. Alternatively, if three or four electrodes are employed, impedance sensor operation and processing circuitry as disclosed in U.S. Pat. No. 4,686,987, issued to Salo et al. or U.S. Pat. No. 4,733,667 issued to Olive et al., respectively, may be employed. All three of these patents are incorporated herein by reference in their entireties. In a fashion analogous to that disclosed in these patents, a sensed increase in the measured arterial volume change (measured impedance change) associated with a heartbeat, absent a corresponding increase in heart rate should be used to trigger an increase in pacing rate by the pacing circuitry 204.

In the event that sensor 200 takes the form a pulse Doppler or transit-time sensor, sensor drive and sensor processing circuitry as described in U.S. Pat. No. 4,598,716 issued to Hileman, incorporated herein by reference, may be employed to create a signal at the output of sensor processing circuitry 202 to be applied as a control signal to pacing circuitry 204. In a fashion analogous to that disclosed in the above cited Koning et al. patent, the measured flow velocity in the adjacent artery may be applied to a look up table to determine an appropriate pacing rate. In general, an increase in peak flow velocity without a corresponding increase in heart rate should indicate an increase in pacing rate.

In the embodiments described above, stress testing of the patent may be employed by the physician to determine the correspondence between sensor output and natural heart rate during conditions of normal heart function. This information may be used by the programmer associated with the pacemaker to generate the look up table for determination of appropriate pacing rates, in a fashion analogous to that disclosed in U.S. Pat. No. 4,867,160, issued to Schaldach and incorporated herein in its entirety. Alternatively, the correspondence between these parameters as derived from a population of patients may be employed to generate look-up tables stored in the pacemaker at time of manufacture.

FIG. 7 illustrates an implantable pacemaker/cardioverter/defibrillator employing the present invention. As discussed above, sensor 208 may take the form of an impedance sensor, a pressure sensor or a pulsatile flow sensor. Pacemaker/cardioverter/defibrillation circuitry 212 may correspond generally to circuitry disclosed in U.S. Pat. No. 4,967,749 issued to Cohen, incorporated herein by reference in its entirety, with some modification. Sensor processing circuitry 210 may correspond to the circuitry discussed in conjunction with sensor processing circuitry 202 in FIG. 6. Pace/sense electrodes 214 may correspond to any prior art cardiac pacing electrodes and CV/defib electrodes 216 may correspond to any known cardioversion/defibrillation electrodes, as discussed in conjunction with FIG. 2, above.

In general, sensor 208 provides a signal to sensor processing circuitry 210 which varies dependant upon the amplitude, presence or absence of pulsatile arterial blood flow. In a fashion analogous to that disclosed in U.S. Pat. No. 3,614,955 issued to Mirowski et al., also incorporated herein by reference in its entirety, cessation of pulsatile flow may be employed as an indication of unstable ventricular tachycardia requiring a cardioversion pulse or of ventricular fibrillation. In a device otherwise disclosed in the cited Cohen patent, therefore, rather than employing short and long term average pressure values, a sufficiently high rate coupled with a pulsatile flow parameter below a predetermined threshold may be used to select between an anti-tachycardia pacing or cardioversion therapy or between a cardioversion pulse and a defibrillation pulse therapy, in the presence of a high rate. Alternatively, a sufficiently high rate in conjunction with an abrupt drop in pulsatile flow from a previously established threshold based on a measured average as disclosed in the cited Cohen patent may instead be employed to select defibrillation rather than cardioversion or cardioversion rather than anti-tachycardia pacing.

While the above disclosures relate to the use of the sensors discussed in the context of implantable pacemakers and implantable pacemaker/cardioverter/defibrillators, it is also believed that venous sensors for monitoring arterial pressure or blood flow may also be usefully employed in the context of an implantable drug dispenser. While not discussed in detail herein, it is envisioned that such sensors may be used to modulate the flow of cardiac drugs on a chronic basis or may be used to initiate the flow of cardiac drugs on an acute basis. Similarly, it is believed that sensors as disclosed in the above application may be employed to provide useful diagnostic information for storage and telemetry to an external receiver, for use by the physician in monitoring and diagnosing the patient's condition. Therefore, the above disclosure should be considered exemplary rather than limiting, rather with regard to the claims that follow. In conjunction with the above specification,

I claim:

1. A method of measuring a parameter of arterial blood flow, comprising:
    positioning at least two electrodes on a transvenous lead body within a vein adjacent to an artery in which it is desired to measure said parameter and measuring variations in impedance between said electrodes due to flow of blood through said artery.

2. A method of measuring a parameter of arterial blood flow, comprising:
    positioning a pressure transducer on a transvenous lead body within a vein adjacent to an artery in which it is desired to measure said parameter and employing said pressure transducer to measure changes in pressure due to blood flow through said artery.

3. A method for regulating the rate of a cardiac pacemaker comprising:
    positioning at least two electrodes on a transvenous lead body within a vein adjacent to an artery and measuring variations in impedance between said electrodes due to flow of blood through said artery.

4. A method for regulating the rate of a cardiac pacemaker comprising:
    positioning a pressure transducer on a transvenous lead body within a vein adjacent to an artery and employing said pressure transducer to measure changes in pressure due to blood flow through said artery.

5. A method of controlling the therapy delivered by an implantable anti-tachycardia device comprising:
    positioning at least two electrodes on a transvenous lead body within a vein adjacent to an artery and measuring variations in impedance between said electrodes due to flow of blood through said artery.

6. A method of controlling the therapy delivered by an implantable anti-tachycardia device comprising:
    positioning a pressure transducer on a transvenous lead body within a vein adjacent to an artery and employing said pressure transducer to measure changes in pressure due to blood flow through said artery.

* * * * *